(12) United States Patent
Knowlton

(10) Patent No.: US 6,311,090 B1
(45) Date of Patent: Oct. 30, 2001

(54) METHOD AND APPARATUS FOR CONTROLLED CONTRACTION OF COLLAGEN TISSUE

(75) Inventor: Edward W. Knowlton, Danville, CA (US)

(73) Assignee: Thermage, Inc., Hayward, CA (US)

( * ) Notice: Subject to any disclaimer, the term of this patent is extended or adjusted under 35 U.S.C. 154(b) by 0 days.

(21) Appl. No.: 09/379,555

(22) Filed: Aug. 23, 1999

Related U.S. Application Data

(63) Continuation of application No. 08/958,305, filed on Oct. 28, 1997, now Pat. No. 5,948,011, which is a continuation of application No. 08/435,822, filed on May 15, 1995, now Pat. No. 5,755,753.

(51) Int. Cl.⁷ ................................................... A61B 18/18
(52) U.S. Cl. .............................. 607/101; 607/102; 606/9; 606/41
(58) Field of Search .............................. 607/96, 98–104, 607/108; 606/2, 9, 33, 41, 50

(56) References Cited

U.S. PATENT DOCUMENTS 5,137,530  *  8/1992  Sand ......................................... 606/5
5,505,730  *  4/1996  Edwards ................................. 606/41
5,569,241  * 10/1996  Edwards ................................. 606/41
5,769,846  *  6/1998  Edwards et al. ....................... 606/41

* cited by examiner

*Primary Examiner*—Roy Gibson
(74) *Attorney, Agent, or Firm*—Wilson Sonsini Goodrich & Rosati

(57) ABSTRACT

A method and apparatus applies radiant energy through the skin to underlying collagen tissue without substantially modifying melanocytes and other epithelial cells in the epidermis. A porous membrane is adapted to receive an electrolytic solution and become inflated to substantially conform a contacting exterior surface of the membrane to a skin layer. The membrane includes a cooling lumen for receiving cooling fluid. One or more thermal electrodes positioned in the membrane and transfers thermal energy to the electrolytic solution. The electrolytic solution and cooling fluid creates a reverse thermal gradient from the skin surface to the underlying collagen tissue. A thermal power source is coupled to the thermal electrodes, and a source of electrolytic solution is coupled to the membrane.

49 Claims, 6 Drawing Sheets

FIG.—3

METHOD AND APPARATUS FOR CONTROLLED CONTRACTION OF COLLAGEN TISSUE

CROSS-REFERENCE TO RELATED CASES

The present application is a continuation of U.S. patent application Ser. No 08/958,305, filed Oct. 28, 1997 now U.S. Pat. No. 5,948,011 which is a continuation of U.S. patent application Ser. No. 08/435,822, filed May 15, 1995 now U.S. Pat. No. 5,755,753 having the same named inventor Edward W. Knowlton.

BACKGROUND OF THE INVENTION

1. Field of the Invention

This invention relates generally to a method and apparatus for shrinking skin tissue without damaging the melanocytes and other epithelial cells, and more particularly to a method and apparatus that creates a reverse thermal gradient in order to achieve skin tightening through partial denaturation of collagen without ablation of the collagen and without affecting the melanocytes and other epithelial cells.

2. Description of Related Art

The skin is the one organ of the body that is readily available for inspection by the eyes and fingers of every living person. It is subjected to considerable abuse such as exposure to extreme environmental of cold, heat, wind, and sun.

The surface layer of the skin is called the epidermis. It is the barrier that prevents most substances from entering the body from outside while preventing body fluids from entering equilibrium with the environment. The basilar layer of the epidermis includes the melanocytes and other epithelial cells.

The melanocytes are small cells with a small, dark staining nucleus and a clear cytoplasm. Melanin packaged in distinctive granules is produced by these cells and transferred to air dendritic processes to adjacent keratinocytes. The purpose of melanin is to protect the skin from the ravages of ultraviolet radiation. Beneath the epidermis is the papillary dermis and reticular dermis. Collagen tissue is found in the dermal and the sub dermal tissues.

There has been a large market for tightening the skin in order to reduce aging effects and effects created by exposing the skin to extreme environmental forces. To date there are two primary methods for tightening skin. The first is surgical skin excision. The second is chemical burn. When skin is surgically excised it leaves large scars. This is generally not a satisfactory solution for many skin tightening applications. With chemical peel treatments the process is painful, there is damage to the melanocytes and other epithelial cells, the patient may have spotted pigmentation, or with most of the melanocytes and other epithelial cells destroyed the patient can have a predominately white complexion. In the chemical peel method a thermal gradient is created which is hotter at the surface of the epidermis and cooler at the sub dermal layers. With the creation of this type of thermal gradient there is a great likelihood of modification or destruction of the melanocytes and other epithelial cells, resulting in blotchiness or an inability to tan in the future.

Collagen molecules are produced by fibroblasts which synthesize three polypeptide chains that wrap around one another in a triple helix. Each of the chains is approximately 1000 amino acid units in length, with glycine recurring regularly every third unit and hydroxyproline and proline recurring very frequently. Cross-linking occurs between the side, not the ends, of collagen molecules and is coupled with the amino acid composition to give collagen its great strength. Collagen tissue shrinkage takes place in a direction parallel to an axis of collagen fibers.

The phenomenon of thermal shrinkage of collagen begins with a denaturization of the triple helix of the collagen molecule. Partial denaturization of collagen tissue results in a shrinkage of the collagen and provides a "tightening" effect on the overlaying skin. To date there have been no devices or methods for contracting the underlying collagen tissue through partial denaturization without damaging the melanocytes and other epithelial cells in the epidermis.

Adipose tissue, more commonly known as fat, is formed of cells containing stored lipid. Adipose tissue is often subdivided into small lobules by connective collagen tissue serving as the fibrous septae.

Adipose tissue is widely distributed in the subcutaneous tissue but exhibits regional differences in amount partially because of age and sex. Excess adipose tissue can be physically undesirable from both health and cosmetic perspective. A current method for the removal of fatty tissue is the extraction of adipose tissue by liposuction. This is a purely mechanical method with undesirable side effects due to the invasive nature of the process.

Another method of removing fatty tissue is disclosed in U.S. Pat. No. 5,143,063 ("the '063"). The method of the '063 patent targets adipose tissue that absorbs sufficient energy resulting in cell destruction and death. The method of the '063 patent fails to minimize damage to the melanocyte in the epidermis. Thus, the method of the '063 patent can create unwanted blotchiness or changes in the melanocytes and other epithelial cells.

There exists the need for skin tightening without damaging the melanocytes and other epithelial cells, or without surgical intervention. There is a further need for non-surgically removing adipose tissue without damaging the melanocytes and other epithelial cells.

SUMMARY OF THE INVENTION

It is an object of the present invention to provide a method and apparatus for tightening skin without substantially damaging the melanocytes and other epithelial cells.

Another object of the present invention is to provide a method and apparatus for tightening skin with the use of a thermal energy source that does not substantially effect the melanocytes and other epithelial cells.

Yet another object of the invention is to provide an inverse thermal gradient from the epidermis to the underlying collagen tissue.

A further object of the invention is to provide a method and apparatus for creating a reverse thermal gradient from the epidermis through a subcutaneous layer of soft tissue.

Still a further object of the present invention is to provide a method and apparatus for tightening skin through the use of an RF energy source and an electrolytic solution which transfer RF energy from RF electrodes to the epidermis and underlying layers.

Yet another object of the present invention is to provide a method and apparatus for creating a reverse thermal gradient that utilizes one or more RF electrodes, an electrolytic solution to transfer RF energy from the RF electrodes to the epidermis and underlying layers, and wherein the apparatus includes a lumen adapted to receive a cooling fluid.

These and other objects of the invention are provided in an apparatus for applying radiant energy through the skin to underlying collagen tissue without substantially modifying melanocytes and other epithelial cells in the epidermis. The apparatus includes a porous membrane adapted to receive an electrolytic solution and become inflated to substantially conform a contacting exterior surface of the membrane to a skin layer. The membrane includes a cooling lumen for receiving a cooling fluid. One or more thermal electrodes are positioned in the membrane and transfer thermal energy to the electrolytic solution. The electrolytic solution and cooling fluid create a reverse thermal gradient from the skin's surface to the underlying collagen tissue. A thermal power source is coupled to the thermal electrodes, and a source of electrolytic solution is coupled to the membrane.

A method for tightening skin comprises providing a membrane in a thermal energy source. A reverse thermal gradient is created which cools the surface of the skin while heating underlying collagen containing layers. The skin and underlying collagen containing tissue are then heated without substantially modifying the melanocytes and other epithelial cells in the epidermis. The result is a contraction of collagen tissue and a tightening of the skin.

Radiant energy is applied to a variety of different skin layers including the papillary dermis layer, the reticular dermis layer, and even to a subcutaneous layer and to underlying soft tissue. One suitable energy source is one or more RF electrodes. Electrolytic solution transfers RF energy from the RF electrodes to the underlying collagen tissue. The cooling fluid can create a reverse thermal gradient at the epidermis to underlying desired layers of about 30 degrees to about 80 degrees C. The apparatus can further include one or more thermal sensors positioned on the contacting exterior surface of the membrane, as well as one or more impedance monitors. Further, the apparatus can include a feedback device which is responsive to a detected characteristic of the skin or subcutaneous layer in order to provide a control delivery of RF energy from the RF electrodes. A variety of detected characteristics can be monitored including impedance measurements of the skin and temperature profiles of the skin.

The feedback device can also include a controller as well as a multiplexer.

The creation of the reverse thermal gradient provides for the controlled contraction of collagen tissue, e.g., partial denaturization of the collagen molecules that results in a shrinkage of the collagen tissue, which then extends to a shrinkage of the skin. Creation of the reverse thermal gradient is different from other methods of collagen contraction which typically employ a thermal gradient that has a higher temperature at the surface and decreases with the depth of penetration.

The apparatus of the present invention that creates the desired contour effect by the modification of collagen tissue surrounding loculations of fat can include a focusing element to help direct the energy past the epidermis and into the fat containing layers. The apparatus can further include a coupling device that couples the focusing element to the membrane, as well as a bracket which is positioned around the periphery of the membrane and also supports the focusing elements. Instead of killing cells, thermal lipolysis is utilized with a cooling blanket on the skin so that thermal destruction fat cells, and the melanocytes and other epithelial cells are minimally damaged.

A variety of thermal energy sources can be employed. Suitable energy sources include but are not limited to RF, microwave, ultrasound and the like. In one embodiment, the preferred energy source is RF.

DETAILED DESCRIPTION

The present invention provides an apparatus for applying radiant energy through the skin to underlying collagen tissue without substantially modifying the melanocytes and other epithelial cells found in the epidermis.

The present invention also provides an apparatus for applying radiant energy through the skin to underlying subcutaneous or deeper soft tissue layers that include loculations of fat with fibrous septae made of collagen tissue. Application of the radiant energy creates a desired contour effect of the loculations of fat without substantially modifying the melanocytes and other epithelial cells in the epidermis. Further, non-invasive methods are provided for skin tightening and tightening the fibrous septae around the loculations of fat to create the desired contour effect.

The methods of the present invention do not provide for total necrosis of cells. Instead, with the method and apparatus creating the desired contour effect, the loculations of fat with the fibrous septae made of collagen tissue use a reverse thermal gradient applied to the underlying collagen tissue layers resulting in a partial denaturization of the collagen permitting it to become tightened. This is achieved without killing all of the fat cells within the loculations.

Various types of radiant energy can be utilized with the present invention. Radiant energy may be any kind that can cause cell heating or physical destruction by being applied to collagen tissue. Examples of suitable radiant energy source include, but are not limited to RF, microwave, ultrasound, and the like.

Figure 1:
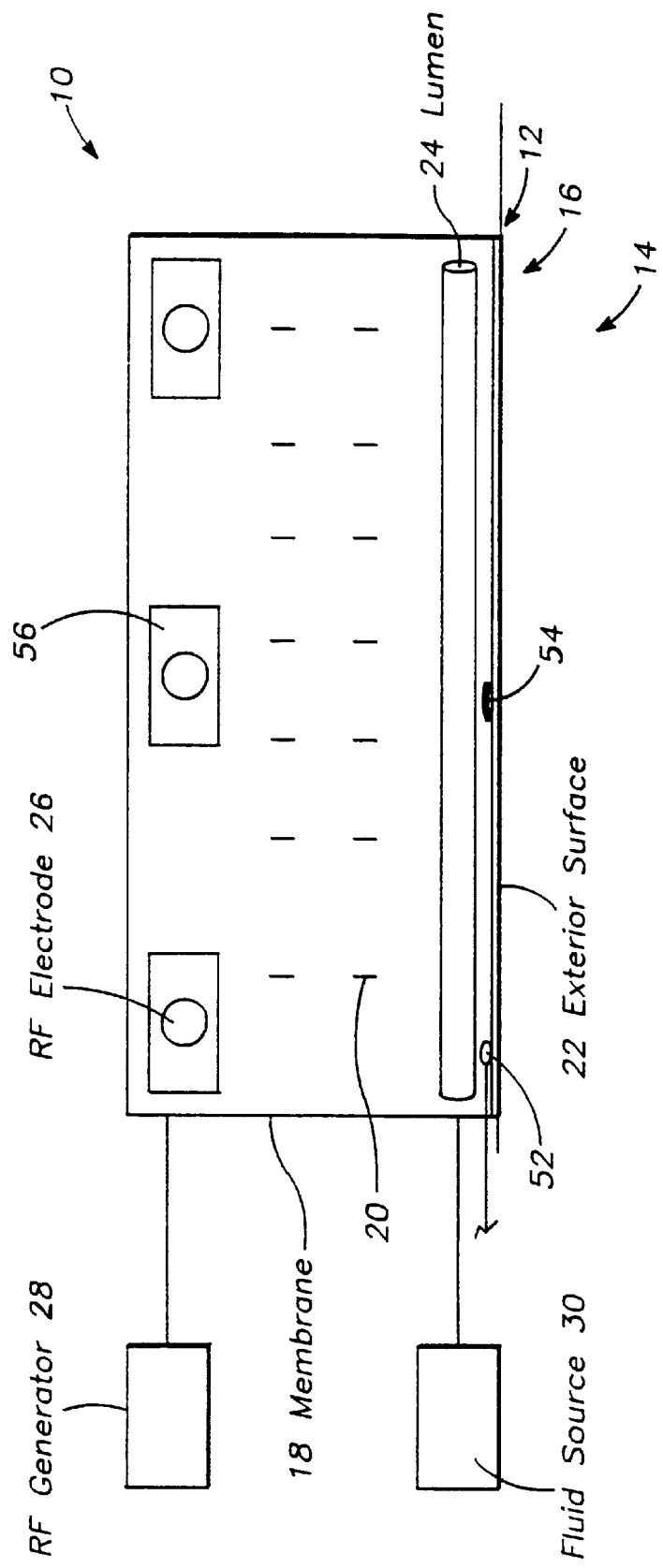
FIG. 1 is a perspective view of an apparatus for applying radiant energy through the skin in order to cause a partial denaturization of collagen tissue, resulting in a tightening of the skin.

Referring now to FIG. 1, an apparatus 10 applies radiant energy through a skin layer 12, such as the epidermis, and to the underlying collagen tissue 14 without substantially modifying melanocytes and other epithelial cells 16 found in the lower layer of epidermis layer 12.

A porous membrane 18 is adapted to receive an electrolytic solution 20. Porous membrane 18 becomes inflated to substantially conform to a contacting exterior surface 22 of porous membrane 18 which is in close thermal contact with epidermis 12. Porous membrane 18 includes a cooling lumen 24 for receiving a cooling fluid that imparts a cooling effect on epidermis layer 12.

One or more thermal electrodes 26 are positioned at various places in porous membrane 18. In one embodiment, thermal electrodes 26 are positioned on a side that is substantially opposing to contacting exterior surface 22. In other embodiments, thermal electrodes 26 are placed closer to cooling lumen 24. In one embodiment particularly suitable for the hips, porous membrane is about 20 cm by 30 cm, with an oval shape.

A thermal power source 28 is coupled to thermal electrodes 26 and a source of electrolytic solution 30 is coupled to porous membrane 18.

Figure 2:
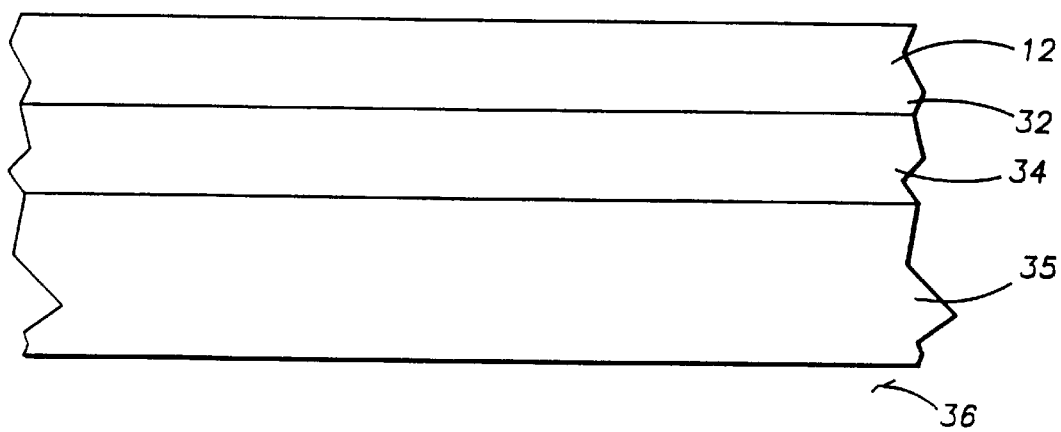
FIG. 2 is a cross-sectional view of the skin and underlying tissue.

With reference now to FIG. 2, radiant energy can be applied through epidermis layer 12, to papillary dermis layer 32, to reticular dermis layer 34, to subcutaneous layer 35, as well as to underlying soft tissue 36. The extent of collage in the various layers is <5% in the epidermis, ~50% in the dermis, ~20% in the subcutaneous, ~5% in the muscle with overlying fascia. Shrinking of collagen tissue takes place in a direction parallel to the axis of the collagen fibers. Thermal shrinkage of collagen begins with the denaturization of the triple helix structure of the collagen fibers. This occurs when thermal energy is applied to the collagen tissue causing the hydrolysis of heat labial cross links of the collagen network.

Figure 3:
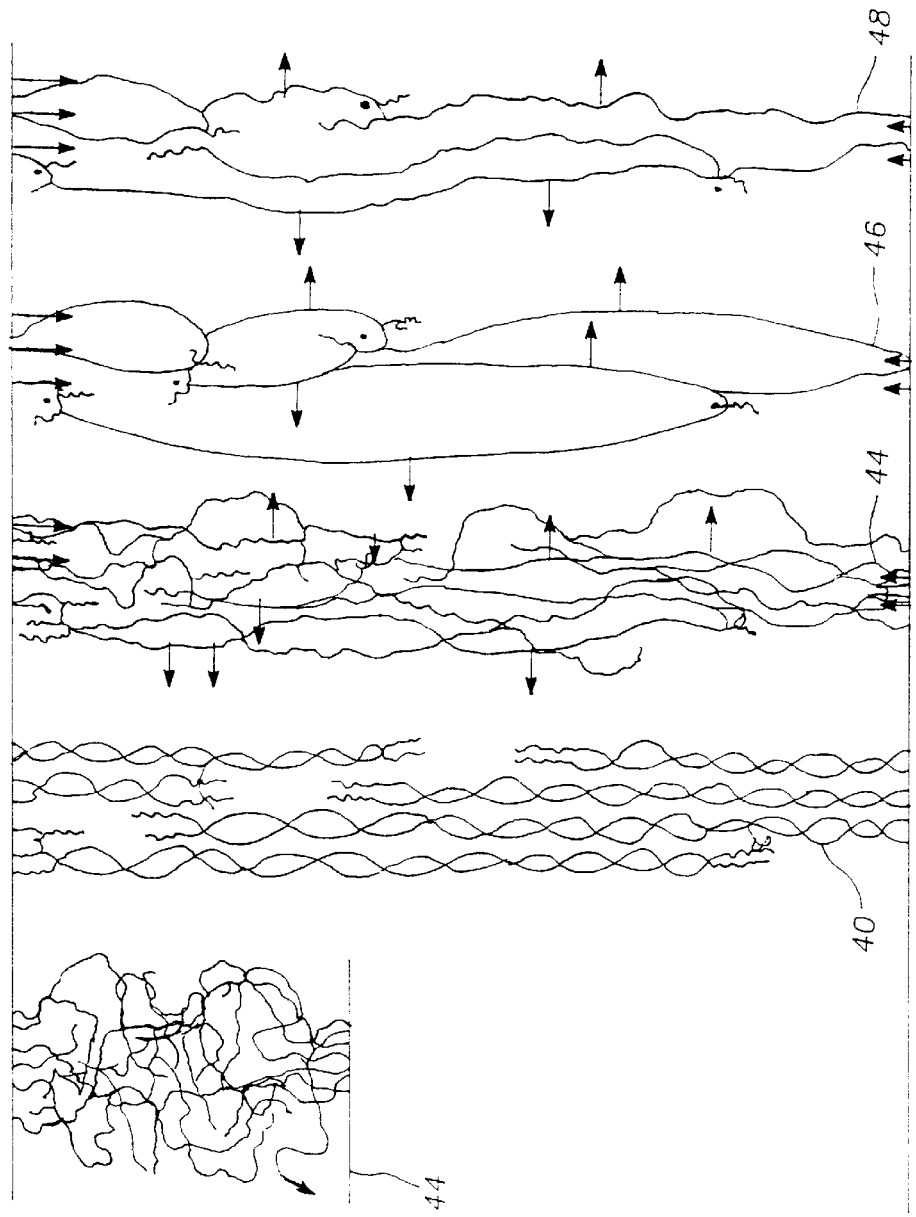
FIG. 3 is a schematic representation of the collagen network.

FIG. 3 is a schematic representation of a collagen network behavior under the influence of heat. The thickened lines represent the chains originally bound by covalent cross links. The arrows indicate tensions exerted on the collagen chains by the effect of heat. More particularly, FIG. 3 illustrates (i). native collagen network 40, (ii). collagen 42 under isometric conditions, (iii). collagen network without any restraint, (iv). collagen network 46 under isometric tension as long as the nodes are stable, and (v). collagen network 48 under isometric tension after some cross links have been cleaved.

In one embodiment of the present invention, thermal electrodes 26 are RF electrodes which can be a single electrode, or a plurality which can form a segmented flexible circuit. Thermal power source 28 is then an RF generator. Electrolytic solution 20 is introduced into porous membrane 18 and passes by RF electrodes 26. Electrolytic solution 20 transfers RF power from RF electrodes 28 to the desired underlying collagen tissue to achieve partial denaturization of the collagen molecule.

Generally, RF electrodes 26 can be monopolar or bipolar. In the monopolar mode, RF current flows through body tissue from a return electrode which can be in a form of a conductive pad applied to the patients outer skin. Maximum heating occurs where the current density is the greatest.

During a treatment phase, the denaturization of collagen molecules can be conducted under feedback control. Treatment can occur without the attention of medical supervision. Feedback is accomplished by (i). visualization, (ii). impedance, (iii). ultrasound, or (iv). temperature measurement. Optionally included and preferably positioned on contacting exterior surface 22 can be one or more thermal sensors 52, as well as one or more impedance monitors 54. Thermal sensors 52 permit accurate determination of the surface temperature of epidermis layer 12.

Electrolytic solution 20 can be preheated to a selected temperature and modified as necessary. This reduces the amount of time needed to effect at satisfactory denaturization of collagen molecules and subsequent skin tightening.

Porous membrane 18 can be made of a material that is an insulator. For purposes of this disclosure, an insulator is a barrier to thermal or electrical energy flow. Porous membrane 18 can be made of a material which permits controlled delivery of electrolytic solution 20 to epidermis layer 12. Porous membrane 18 can be made of a variety of materials including, but not limited to knitted polyester, continuous filament polyester, polyester-cellulose, rayon, polyamide, polyurethane, polyethylene and the like. Suitable commercial products include, (i). Opcell available from Centinal Products Corp., Hyannis, Mass., and (ii). UltraSorb, HC 4201 or HT 4644 MD from Wilshire Contamination Control, Carlsbad, Calif. Pockets or zones 56 can be formed around RF electrodes 26. Each pocket 56 has a lower porosity for the flow of electrolytic solution 20 than all other sections of porous membrane 18. Differences in porosity can be achieved with different types of materials which form porous membrane 18. Electrolytic solution 20 is retained in pockets 56 longer than in non-pocket sections of 18, and there is a greater transfer of RF energy to electrolytic solution 20, creating a larger electrode. The larger electrode produces RF and thermal energy to create a larger electrode effect. However, this does not effect the creation of the reverse thermal gradient. RF energy is still transferred through porous membrane 18 passing in the vicinity of cooling lumen 24, in order to create a lower temperature at epidermis layer 12 and the temperature increases as deeper layers are reached.

Figure 4:
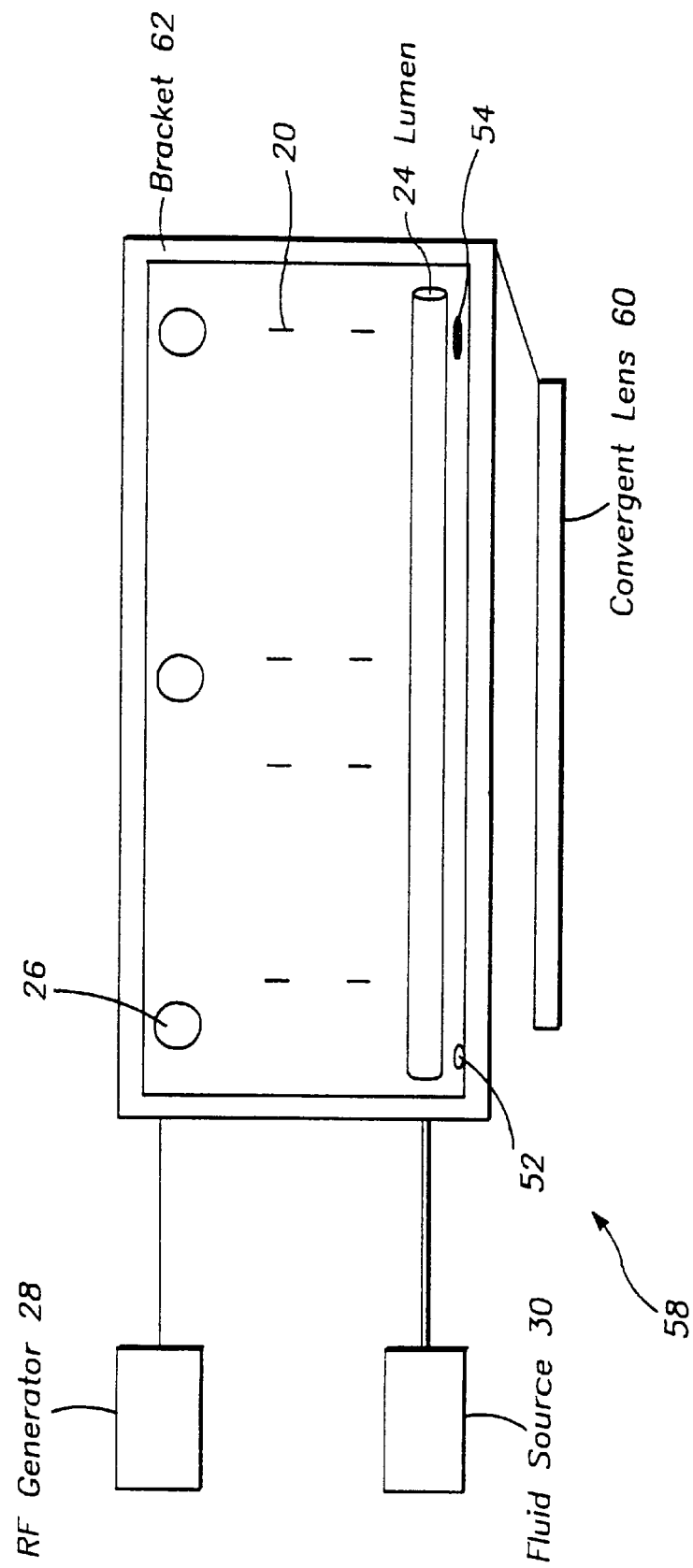
FIG. 4 is a schematic diagram of an apparatus for applying radiant energy to underlying subcutaneous layers or deeper soft tissue layers to create a desired contour effect by partially denaturing collagen tissue, and without substantially modifying melanocytes and other epithelial cells in the epidermis.
Figure 5:
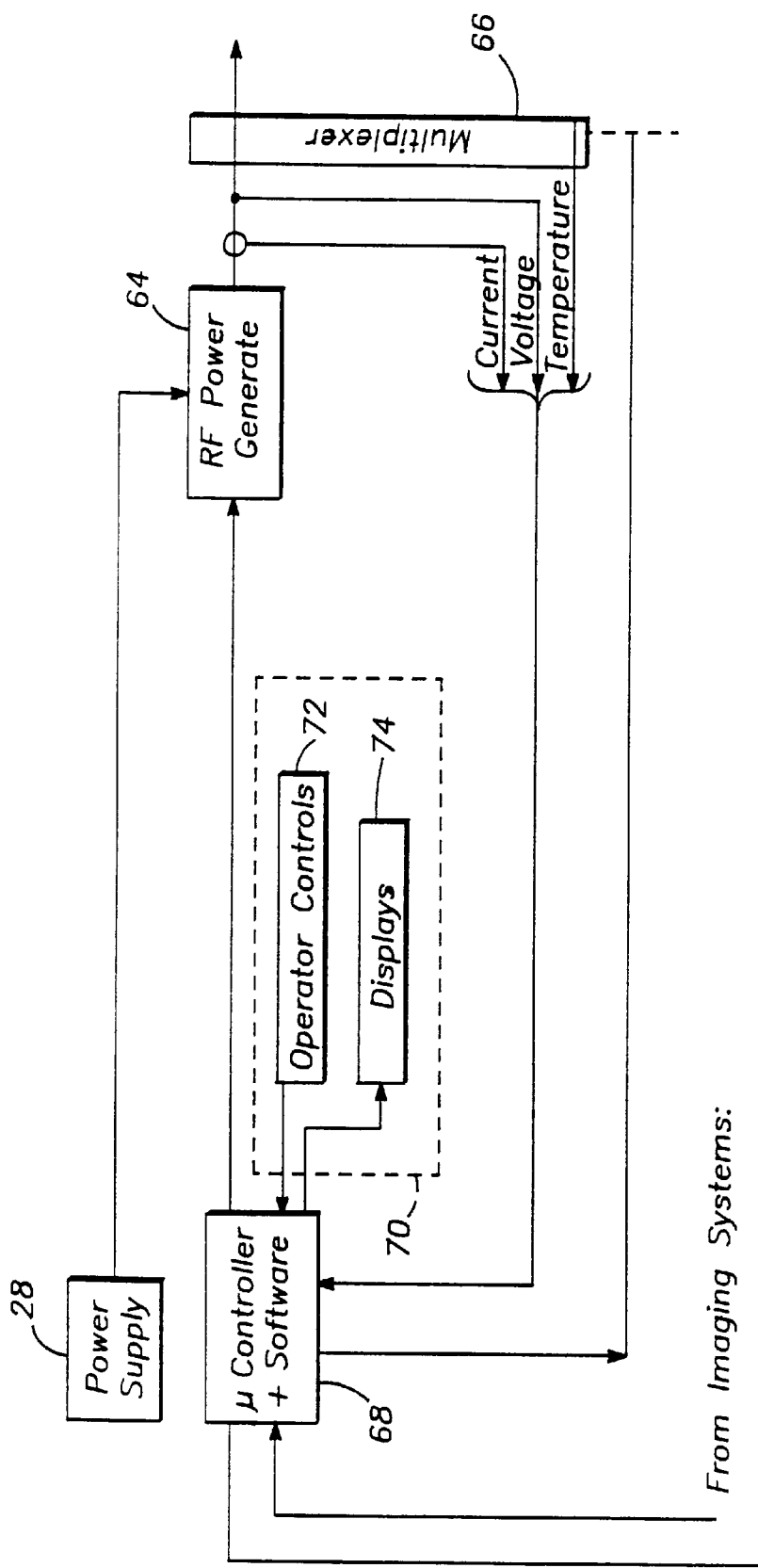
FIG. 5 is a block diagram of an RF system which can be utilized with the present invention.

Referring now to FIG. 4, an apparatus 58 for creating a desired contour effect of underlying subcutaneous layers or deeper soft tissue layers which include loculations of fat with fibrous septae made of collagen tissue is illustrated. The apparatus 58 of FIG. 4, includes a 18, electrolytic solution 20, a contacting exterior surface 22, a cooling lumen, thermal electrodes 26, a thermal power source 28, an electrolytic solution source 30, one or more thermal sensors 52, as well as one or more impedance monitors 54. Apparatus 58 also includes a focusing element 60 which focuses thermal energy from electrolytic solution 20 to the underlying collagen tissue. Focusing element 60 and electrolytic solution 20 create a reverse thermal gradient from epidermis layer 12 to the underlying collagen tissue 14. Focusing element 60 can be, in the case of ultrasonic energy, a lens having a flat planar surface on the radiation wave incident side and a concave exit face, see *Ultrasonics Theory and Application*, by G. L. Gobennan, Heart Publishing Co., New York (1959), at section 2.6. The use of such a focussing lens for ultrasonic energy with a planer wave receiving face and concave exit face is also described in the article "Deep Local Hypothermia for Cancer Therapy: Extreme Electromagnetic and Ultrasound Technics," A. Y. Cheung and A. Neyzari, *Cancer Research*, Vol. 44, pp.4736–4744, October 1984.

Radio frequencies can be the thermal energy source, and various localizing techniques, well-known in the art, can be utilized. In one embodiment, radio frequency energy is supplied by capacitive coupling directly to epidermis layer 12 for areas close to the dermal tissue. Radio frequency induction focusing can be achieved with the use of plural focusing coils which are adaptive at the zone of interest and are elsewhere subtractive. Alternatively, radio frequency energy may be focused by having a multiple beam phased array. For concave focusing see, "Tumor reduction by radio frequency therapy response", H. H. Lavien et al., *JAMA*, Vol. 233, at 2198–2200.

Alternative radio frequency focusing methods are disclosed in "Equipment for Local Hypothermia Therapy of Cancer", C. F. Babbs et al., *Medical Instrumentation*, Vol. 16, No. 5, September –October 1982, pp. 245–248.

It will be appreciated that focusing element 60 can be a convergent lens. Further, focusing element 60 can be positioned in porous membrane 18, and at the exterior 16 between epidermis layer 12 and porous membrane 18. Further, a coupling device 62 can be included which couples focusing element 60 with porous membrane 18. In one embodiment, coupling device 62 is a bracket which is positioned around a periphery of porous membrane 18, and supports focusing element 60 in relation to porous membrane 18.

In the method for tightening skin, porous membrane 18 and thermal energy source 26 are provided. A reverse thermal gradient is created which cools a surface of epidermis layer 12 while heating underlying collagen containing layers. Epidermis layer 12 as well as underlying collagen containing tissue are heated, without substantially affecting the melanocytes and other epithelial cells in epidermis layer 12, resulting in a denaturization of collagen molecules, causing a contraction of the collagen tissue and a tightening of the skin. This method can be applied numerous times. In many instances, it may be desirable to tighten the skin to a certain level and then in subsequent treatments the skin is tightened further. There may be four fine treatments to fine tune the contour effects with greater precision. In this method, collagen containing tissue is partial denatured and fat cell destruction is minimized. This is achieved by partially denaturing by cleaving heat labial cross links of the collagen molecules.

The reverse thermal gradient provides a variation in temperature throughout the various tissue layers. For example, in one embodiment, the reverse thermal gradient is a temperature range from about 30 degrees to about 80 degrees C, initiating from epidermis layer 12 to collagen containing tissue layers. The reverse thermal gradient can have a temperature range of about 30 to 75 degrees C, and additionally from about 0.30 to 70 degrees C.

In another embodiment, a method for liposculpturing an area of the body where there is an underlying area comprised of a loculation of fat that has collagen tissue as a fibrous septae also includes creating a reverse thermal gradient from epidermis layer 12 to the desired underlying loculation of fat layer. Sufficient thermal energy is supplied through epidermis layer 12, without damaging or substantially modifying the melanocytes and other epithelial cells, through other skin layers and is focused on the collagen tissue of the fibrous septae. Thermal energy partially denatures the collagen tissue with a minimal destruction of fat cells. Again, this is achieved by partially denaturizing, e.g., by cleaving, heat labial cross links of collagen molecules. The reverse thermal gradient produces a net mobilization of intra-cellular fat with diminished destruction of fat cells.

For purposes of illustration, without the scope of the invention let it be assumed that power source 28 is an RF power source, an RF power source 28, feeds energy to an RF power generator 64 and then to RF electrodes 26. A multiplexer 66 measures current, voltage and temperature, at the numerous thermal sensors associated to each RF electrode 26. RF electrodes 26 can be individually measured. Multiplexer 66 is driven by a controller 68 which can be a digital or analog controller, or a computer with software. When controller 68 is a computer it can include a CPU coupled through a system bus. The system can be a keyboard, disk drive, or other nonvolatile memory systems, a display, and other peripherals, as are well known in the art. Also coupled to the bus are a program memory and a data memory.

An operator interface 70 includes operator controls 72 and a display 74. Controller 68 can be coupled to different types of imaging systems including ultrasonic, thermal sensors 52, and impedance monitors 54.

Current and voltage are used to calculate impedance. A diagnostic phase can be initially run to determine the level of treatment activity. This can be done through ultrasound as well as other means. Diagnostics can be performed both before and after treatment.

Thermal sensors 52, and thermal sensors 76 contained within RF generator 64 measure voltage and current that is delivered to the desired treatment site. The output for these sensors is used by controller 68 to control the delivery of RF power. Controller 68 can also control temperature and power. An operator set level of power and/or temperature may be determined and this will not be exceeded. Controller 68 maintains the set level under changing conditions. The amount of RF energy delivered controls the amount of power. A profile of power delivered can be incorporated in controller 68, as well as a preset amount of energy to be delivered. Feedback can be the measurement of impedance, temperature, or other indicators and occurs either at control 68 or at RF generator 64, if it incorporates a controller. For impedance measurement, this can be achieved by supplying a small amount of nontherapeutic RF energy. Voltage and current are then measured to confirm electrical contact.

Circuitry, software and feedback to controller 68 result in fill process control and are used to change, (i). power, (ii). the duty cycle, (iii). monopolar or bipolar energy delivery, (iv). electrolytic solution 20 delivery, flow rate and pressure and (v). can determine when the process is completed through time, temperature and/or impedance. These process variables can be controlled and varied based upon tissue temperature monitored at multiple sites on contacting exterior surface 22 as well as monitoring impedance to current flow at each RF electrode 26, indicating changes in current carrying capability of the tissue during the process. Further, controller 68 can provide multiplexing, monitor circuit continuity, and determine which RF electrode 26 is activated.

Figure 6:
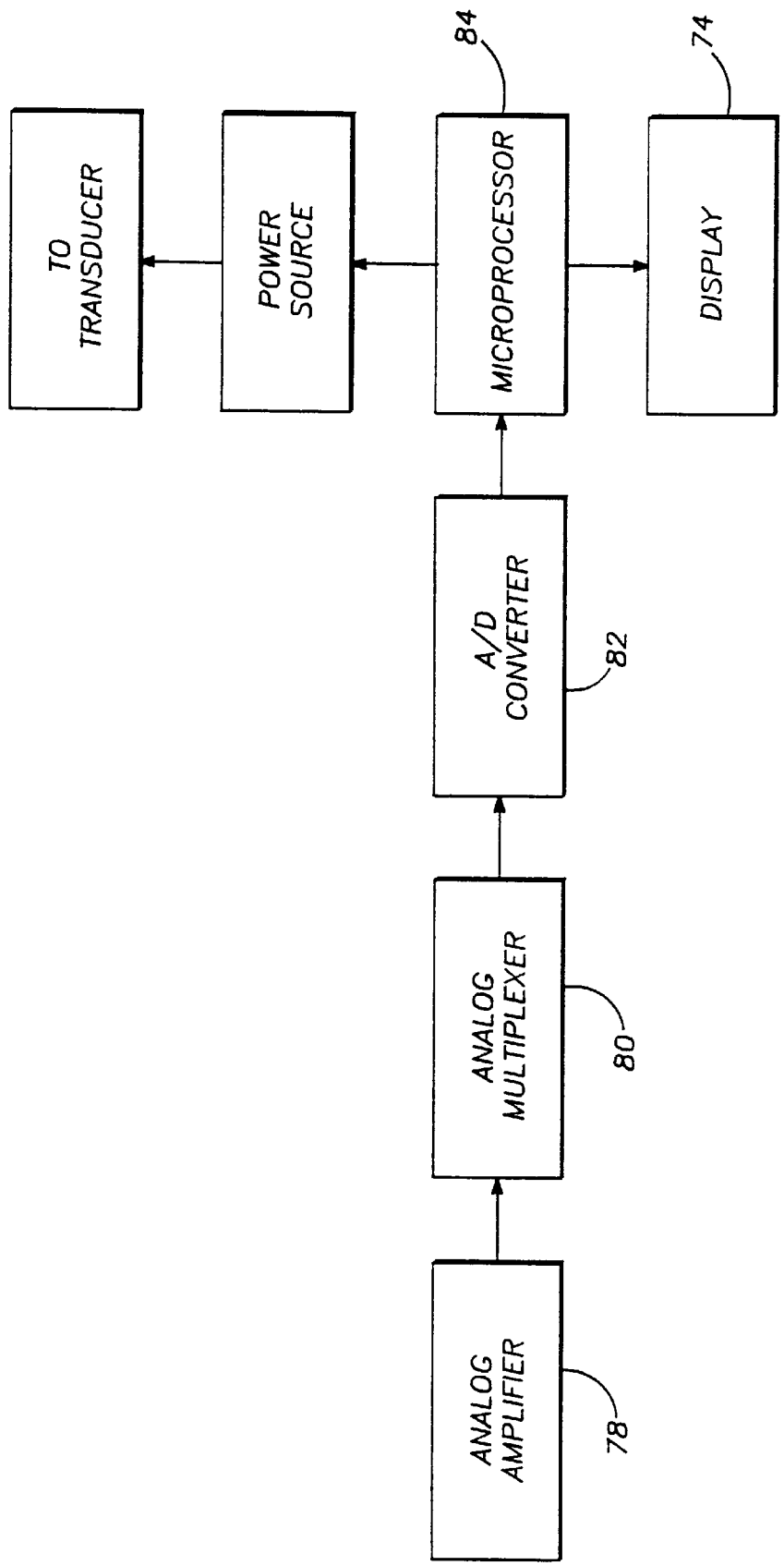
FIG. 6 is a block diagram of a processing circuit of one embodiment of the invention.

A block diagram of one embodiment of suitable processing circuitry is shown in FIG. 6. Thermal sensors 52 can be thermistors which have a resistance that varies with temperature. Analog amplifier 78 can be a conventional differential amplifier circuit for use with thermistors and transducers. The output of analog amplifier is sequentially connected by an analog multiplexer 80 to the input of an analog digital converter 82. The output of amplifier 78 is a voltage which represents the respective sensed temperatures. The digitized amplifier output voltages are supplied by analog to digital converter 82 to a microprocessor 84. Microprocessor 84 calculates the temperature or impedance of the tissue. Microprocessor 84 can be a type 6800. However, it will be appreciated that any suitable microprocessor or general purpose digital or analog computer can be used to calculate impedance or temperature.

Microprocessor 84 sequentially receives and stores digital representations of impedance and temperature. Each digital value received by microprocessor 84 corresponds to different temperatures and impedances.

Calculated temperature and impedance values can be indicated on display 74. Alternatively, or in addition to the numerical indication of temperature or impedance, calculated impedance or temperature values can be compared by microprocessor 84 with temperature and impedance limits. When the values exceed predetermined temperature or impedance values a warning can be given on display 74 and additionally, the delivery of RF energy to its respective electrode can be decreased or multiplexed to another electrode. A control signal from microprocessor 84 can reduce the power level by RF generator 64, or de-energize the power delivered to any particular electrode. Controller 68 receives and stores the digital values which represent temperatures and impedances sent. Calculated surface temperatures and impedances can be forwarded by controller 68 to display 74. If desired, the calculated surface temperature of epidermis layer 12 is compared with a temperature limit and a warning signal can be sent to display 74. Similarly, a control signal can be sent to RF power source 26 when temperature or impedance values exceed a predetermined level.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An apparatus for tightening a skin surface overlying a collagen containing tissue site comprising:
    a porous membrane having an inflated and a non inflated state, the porous membrane adapted and receive, be at least partially inflated by and controllably release an electrolytic solution, the porous membrane having a tissue contacting surface conformable to at least a portion of the skin surface while in the inflated state;
    a cooling lumen disposed within the porous membrane, the lumen adapted to receive a cooling fluid and provide a cooling effect to an epidermal layer substantially overlying a collagen containing tissue layer; and
    an energy delivery device coupled to the porous membrane, the energy delivery device configured to deliver energy to one of the electrolytic solution or the collagen containing tissue site, the energy delivery device configured to be coupled to a power source.

2. The apparatus of claim 1, wherein at least a portion of the porous membrane includes one of a fibrous material, a hydrophobic material or a foam material.

3. The apparatus of claim 1, further comprising an electrolytic fluid source fluidically coupled to the porous membrane.

4. The apparatus of claim 1, further comprising an fluid source fluidically coupled to the cooling lumen.

5. The apparatus of claim 1, further comprising a power source coupled to the energy delivery device.

6. The apparatus of claim 5, further comprising a feedback control device electronically coupled to at least one of the sensor, a power source, the energy delivery device, or a multiplier.

7. The apparatus of claim 1, further comprising: a sensor coupled to the porous membrane.

8. The apparatus of claim 7, wherein the sensor is coupled to the tissue contacting surface.

9. The apparatus of claim 7, wherein the sensor is one of a thermal sensor or an impedance sensor.

10. The apparatus of claim 7, wherein the sensor is configured to a measure a thermal property of the epidermal layer.

11. The apparatus of claim 7, wherein the feedback control device includes one of an electronic controller or a multiplier, multiplexed to at least one of the sensors or the energy delivery devices.

12. The apparatus of claim 1, wherein the electrolytic solution is configured to deliver energy to the collagen containing tissue layer.

13. The apparatus of claim 1, wherein the electrolytic solution is configured to deliver sufficient energy to the collagen containing tissue layer to cause at least a partial denaturization of at least a portion of collagen in the collagen containing a layer.

14. The apparatus of claim 12, wherein at least one of the cooling fluid, the electrolytic fluid or the energy delivery device is configured to produce a reverse thermal gradient, with a temperature of at least a portion of the epidermal layer less than a temperature of a least a portion of the underlying the collagen containing tissue layer.

15. The apparatus of claim 14, wherein the reverse thermal gradient is sufficient to minimize a thermal injury of the tissue site including one of a cell necrosis, a fat cell necrosis, an epithelial cell modification or a melanocyte modification.

16. The apparatus of claim 14, wherein the reverse thermal gradient is about 30° C. to about 80° C.

17. The apparatus of claim 1, wherein the energy delivery device is an RF electrode configured to be coupled to an RF power source.

18. The apparatus of claim 17, wherein the RF electrode is one of a monopolar or a bipolar electrode.

19. The apparatus of claim 17, wherein the RF electrode transfers RF energy to the electrolytic solution and the electrolytic solution delivers energy to the tissue site.

20. The apparatus of claim 17, wherein the RF electrode is a plurality of electrodes.

21. The apparatus of claim 20, wherein the plurality of electrodes comprises a flexible circuit.

22. The apparatus of claim 20, wherein at least one of the plurality of electrodes is multiplexed to an RF power source.

23. The apparatus of claim 20, further comprising:
    a sensor positioned substantially adjacent to at least one of the plurality of RF electrodes and the sensor is multiplexed to a feedback control device.

24. The apparatus of claim 20, wherein the at least a portion of the plurality of RF electrodes is a phased array.

25. The apparatus of claim 17, wherein the RF electrode comprises at least one coil configured to focus RF energy at a selectable depth beneath the skin surface.

26. The apparatus of claim 17, wherein the membrane has a substantially oval shape.

27. The apparatus of claim 17, wherein the porous membrane has a non-tissue contacting surface opposing the tissue contact surface and the RF electrode is substantially positioned on the non-tissue contacting surface.

28. The apparatus of claim 17, wherein the membrane further comprises:
    at least one zone of increased porosity; and
    a remainder membrane portion having a lower porosity relative to the zone of increased porosity.

29. The apparatus of claim 28, wherein the at least one zone of increased porosity is configured to at least partially retain a portion of the electrolytic solution for a longer time period than the remainder membrane portion.

30. The apparatus of claim 29, wherein energy transfer to the portion of electrolytic solution is enhanced.

31. The apparatus of claim 29 wherein the RF electrode is substantially disposed within the at least one zone of increased porosity.

32. The apparatus of claim 29, wherein the portion of the electrolytic solution functions as an RF electrode.

33. The apparatus of claim 1, further comprising:
    a focusing element coupled to the membrane, the focusing element configured to focus energy at a selectable depth beneath the skin surface.

34. The apparatus of claim 33, further comprising: a coupling device coupled to at least one of the focusing element or the membrane, the coupling device configured to couple the focusing element to the membrane.

35. The apparatus of claim 1, wherein the porous membrane has one of a variable porosity or a variable electrical resistance.

36. The apparatus of claim 35, wherein the porosity of the membrane varies over at a least a portion of an area of the membrane.

37. The apparatus of claim 1, wherein the energy device is an acoustical transducer.

38. The apparatus of claim 1, wherein the energy device is a microwave antenna configured to be coupled to a microwave power source.

39. The apparatus of claim 1, wherein the energy delivery device is a waveguide configured to be coupled to a light source.

40. The apparatus of claim 39, wherein the light source is a coherent light source.

41. An apparatus for tightening a skin surface overlying a collagen containing tissue site comprising:

a porous membrane having an inflated and a non inflated state, the porous membrane adapted to receive and be at least partially inflated by an electrolytic solution, the porous membrane having higher porosity zone and a lower porosity zone, and a conformable tissue contacting surface configured to be conformable to at least a portion of the skin surface while in the inflated state;

a cooling lumen disposed within the porous membrane, the lumen adapted to receive a cooling fluid and provide a cooling effect to an epidermal layer at substantially overlying a collagen containing tissue layer; and an energy delivery device coupled to the porous membrane, the energy delivery device configured to deliver energy to one of the electrolytic solution or the collagen containing tissue site, the energy delivery device configured to be coupled to a power source.

42. The apparatus of claim 41, further comprising an electrolytic fluid source fluidically coupled to the porous membrane.

43. The apparatus of claim 41, further comprising a fluid source fluidically coupled to the cooling lumen.

44. The apparatus of claim 41, further comprising a power source coupled to the energy delivery device.

45. The apparatus of claim 41, further comprising:

a sensor coupled to the porous membrane.

46. The apparatus of claim 45, wherein the sensor is coupled to the tissue contacting surface.

47. The apparatus of claim 45, wherein the sensor is one of a thermal sensor or an impedance sensor.

48. The apparatus of claim 45, wherein the sensor is configured to a measure a thermal property of the epidermal layer.

49. The apparatus of claim 45, further comprising a feedback control device electronically coupled to al least one of the sensor, a power source, the energy delivery device, or a multiplier.

* * * * *

UNITED STATES PATENT AND TRADEMARK OFFICE
CERTIFICATE OF CORRECTION

PATENT NO. : 6,311,090 B1
DATED : October 30, 2001
INVENTOR(S) : Knowlton

It is certified that error appears in the above-identified patent and that said Letters Patent is hereby corrected as shown below:

<u>Title page,</u>
Item [56], References Cited, please insert the following:
-- U.S. PATENT DOCUMENTS

| | | | |
|---|---|---|---|
| 3,831,604 | 8/1974 | Neefe ……………… | 128/260 |
| 4,074,718 | 11/1978 | Morrison……………… | 128/303.14 |
| 4,140,130 | 2/1979 | Storm, III……………... | 128/404 |
| 4,164,226 | 8/1979 | Tapper ……………… | 128/419 R |
| 4,290,435 | 8/1981 | Waggott………………. | 128/800 |
| 4,343,301 | 8/1982 | Indech ……………... | 128/24 |
| 4,346,715 | 8/1982 | Gammell ……………... | 128/422 |
| 4,375,220 | 5/1983 | Matvias……………… | 128/804 |
| 4,381,007 | 4/1983 | Doss ………………… | 128/303.1 |
| 4,441,486 | 4/1984 | Pounds……………….. | 128/4 |
| 4,545,368 | 10/1985 | Rand et al…………….. | 128/1.3 |
| 4,676,258 | 6/1987 | Inokuchi et al…………. | 128/804 |
| 4,709,701 | 12/1987 | Weber……………… | 128/422 |
| RE 32,849 | 1/1989 | Wei et al………………. | 204/192.27 |
| 4,881,543 | 11/1989 | Trembly et al………… | 128/303.1 |
| 4,887,614 | 12/1989 | Shirakami et al……….. | 128/798 |
| 4,889,122 | 12/1989 | Watmough et al ………. | 128/399 |
| 4,944,302 | 7/1990 | Hernandez et al……….. | 128/798 |
| 4,957,480 | 9/1990 | Morenings……………. | 604/20 |
| 4,962,761 | 10/1990 | Golden……………….. | 128/400 |
| 4,976,709 | 10/1990 | Sand………………….. | 606/5 |
| 5,003,991 | 4/1991 | Takayama et al……….. | 128/784 |
| 5,133,351 | 7/1992 | Masaki……………….. | 128/419 R |

UNITED STATES PATENT AND TRADEMARK OFFICE
CERTIFICATE OF CORRECTION

PATENT NO.    : 6,311,090 B1
DATED         : October 30, 2001
INVENTOR(S)   : Knowlton It is certified that error appears in the above-identified patent and that said Letters Patent is hereby corrected as shown below:

Item [56], References Cited,

U.S. PATENT DOCUMENTS (cont'd,)

| | | | |
|---|---|---|---|
| 5,143,063 | 9/1992  | Fellner        | 128/399 |
| 5,186,181 | 2/1993  | Franconi et al.| 128/804 |
| 5,190,517 | 3/1993  | Zieve          | 604/22  |
| 5,230,334 | 7/1993  | Klopotek       | 128/399 |
| 5,249,575 | 10/1993 | DiMino et al.  | 607/150 |
| 5,282,797 | 2/1994  | Chess          | 606/9   |
| 5,304,169 | 4/1994  | Sand           | 606/5   |
| 5,315,994 | 5/1994  | Guibert et al. | 607/101 |
| 5,334,193 | 8/1994  | Nardella       | 606/41  |
| 5,342,357 | 8/1994  | Nardella       | 606/40  |
| 5,348,554 | 9/1994  | Imran et al.   | 606/41  |
| 5,370,642 | 12/1994 | Keller         | 606/9   |
| 5,374,265 | 12/1994 | Sand           | 606/5   |
| 5,423,807 | 6/1995  | Milder         | 606/20  |
| 5,423,811 | 6/1995  | Imran et al    | 606/41  |
| 5,437,662 | 8/1995  | Nardella       | 606/40  |
| 5,458,596 | 10/1995 | Lax et al.     | 606/31  |
| 5,462,521 | 10/1995 | Brucker et al. | 604/20  |
| 5,464,436 | 11/1995 | Smith          | 607/89  |
| 5,496,312 | 3/1996  | Klicek         | 606/34  |
| 5,507,790 | 4/1996  | Weiss          | 607/100 |
| 5,569,242 | 10/1996 | Lax et al.     | 606/42  |
| 5,660,836 | 10/1996 | Knowlton       | 606/101 |
| 5,755,753 | 5/1998  | Knowlton       | 606/101 |

UNITED STATES PATENT AND TRADEMARK OFFICE
CERTIFICATE OF CORRECTION

PATENT NO.     : 6,311,090 B1
DATED          : October 30, 2001
INVENTOR(S)    : Knowlton It is certified that error appears in the above-identified patent and that said Letters Patent is hereby corrected as shown below:

Item [56], References Cited,

FOREIGN PATENT DOCUMENTS

| | | |
|---|---|---|
| 1949534 | 4/1970 | Germany |
| 2609245 | 7/1988 | France |
| 3121683 | 12/1982 | Germany |
| 92/19414 | 11/1992 | PCT |
| 0519415 | 12/1992 | Europe |
| 96/34568 | 11/1996 | PCT |

OTHER PUBLICATIONS

Allain, et al., "Isometric Tensions Developed During the Hydrothermal Swelling of Rat Skin", Connective Tissue Research, vol 7, pp. 697-701, (1990).
Danielson, C.,"Age-Related thermal stability and susceptibility to proteolysis of rat bone collagen", ....chem, Great Britain, pp. 697-701, (1990).
Danielson, C.,"Thermal stability of reconstituted collagin fibrils, shrinkage characteristics upon in vitro maturation", Mechanisms of Ageing and Development, Vol. 15, pp. 269-278, (1981).
Kronick, et al.,"The locations of collagens with different thermal stabilities in fibrils of bovine recticular dermis".
Connective Tissue Research, Vol. 18, pp. 123-134, (1988).
Mainster, M.A., "Ophthalmic applications of infrared lasers - thermal considerations", Visual Sci., pp. 414-420, April 1979.
Pearce, et al. "Kinetic models of laser-tissue fusion processes", ISA, paper #93-044, pp. 355-360, (1993).
Adrian, R.M., "Treatment of Facial Telangiectasia Using the VersaPulse® Variable Pulse Width Frequency Doubled Neodymium: YAG Laser: A Case Report.
Chess, C.; Chess, Q., "Cool Laser Optics Treatment of Large Telangiestasia of the Lower Extremities", *J. Dermatol Surg Oncol*. 1993; 19:74-80.

UNITED STATES PATENT AND TRADEMARK OFFICE
CERTIFICATE OF CORRECTION

PATENT NO. : 6,311,090 B1
DATED : October 30, 2001
INVENTOR(S) : Knowlton

It is certified that error appears in the above-identified patent and that said Letters Patent is hereby corrected as shown below:

OTHER PUBLICATIONS (cont'd)

Coulson, W.F. et al., "Nonablative Laser Treatment of Facial Rhytides: Animal Study."
Abstract for BiOS '98 Symposium Conference: bo05 - Cutaneous Applications of Lasers, 24-30, January 1998, San Jose, CA. Kincade, K. ,"Demand for Laser Resurfacing Soars: Quicker Healing, Less Risk of Scarring" *Dermatology Times.* 1995. 16(10)
Fitzpatrick, R., "Treatment of Wrinkles with the UltraPulse $CO_2$ Laser."
Laser Aesthetics, Inc. "The Cool Touch Laser." Brochure.
Laser Aesthetics, Inc. "Cool Touch Model 130 Technical Specifications." Brochure.
National Health Communications, Inc. "New Laser Eliminates 'Lipstick Bleed'" Press Release July 1993. --

Signed and Sealed this

Sixth Day of August, 2002

*Attest:*

*Attesting Officer*

JAMES E. ROGAN
*Director of the United States Patent and Trademark Office*